United States Patent [19]
Okada et al.

[11] Patent Number: 5,264,417
[45] Date of Patent: Nov. 23, 1993

[54] THERAPEUTIC TREATMENT FOR SWINE PLEUROPNEUMONIA

[75] Inventors: Masaaki Okada, Tsukuba; Shigeyoshi Ura, Kyoto; Satoru Nakano, Tsuchiura, all of Japan

[73] Assignee: Fujisawa Pharmaceutical Co., Ltd., Osaka, Japan

[21] Appl. No.: 890,404

[22] Filed: May 29, 1992

[30] Foreign Application Priority Data

Jun. 4, 1991 [JP] Japan .................. 3-230722

[51] Int. Cl.$^5$ ............................. A61K 37/10
[52] U.S. Cl. .................................... 514/8
[58] Field of Search ............... 514/8; 540/456

[56] References Cited

U.S. PATENT DOCUMENTS

| | | | |
|---|---|---|---|
| 3,923,790 | 12/1975 | Imanaka et al. | 540/456 |
| 4,145,344 | 3/1979 | Muller et al. | 540/456 |
| 4,209,518 | 6/1980 | Mine et al. | 424/250 |
| 4,215,043 | 7/1980 | Kamiya et al. | 540/456 |

FOREIGN PATENT DOCUMENTS 48-39497  6/1973  Japan .

*Primary Examiner*—Frederick E. Waddell
*Assistant Examiner*—K. Weddington
*Attorney, Agent, or Firm*—Oblon, Spivak, McClelland, Maier & Neustadt

[57] ABSTRACT

This invention relates to a novel prophylactic/-therapeutic agent for the treatment of swine pleuropneumonia which comprises a bicozamycin ester represented by the following formula

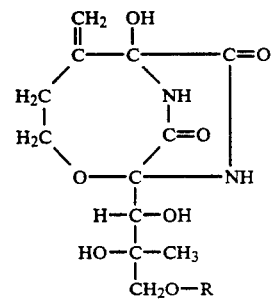

wherein R means a benzoyl group or a cyclohexanecarbonyl group.

2 Claims, No Drawings

THERAPEUTIC TREATMENT FOR SWINE PLEUROPNEUMONIA

The present invention relates to a novel prophylactic/therapeutic agent for swine pleuropneumonia and more particularly to a prophylactic/therapeutic composition for swine pleuropneumonia which comprises a bicozamycin ester represented by the following formula (I):

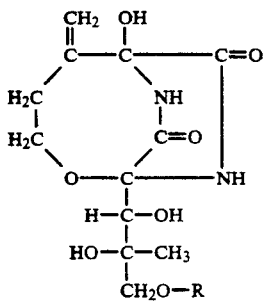

(wherein R means a benzoyl group or a cyclohexanecarbonyl group).

Swine pleuropneumonia is an infectious disease which about 60 percent of farmed hogs are estimated to contact during their lifetimes and the resulting fatalities and decreased feed efficiencies taken together amount to significant economic losses.

Heretofore, in the prevention and treatment of swine pleuropneumonia, antibiotics such as ampicillin, oxytetracycline, etc. have been administered parenterally or orally according to the prevailing condition but the above-mentioned high infection rate indicates that this disease can not be completely cured with the conventional antibiotics. The reason is generally believed to be as follows.

The causative agent of this disease, *Actinobacillus pleuropneumoniae*, is a resident organism in the nasal cavity of hogs and once the disease develops as triggered by various stresses and forms lesions accompanied by fibrous induration in the lungs at short notice, the causative bacteria keep dwelling in the induration tissue to cause recurrences at the first oppertunities.

The use of conventional antibacterial agents is not sufficient to arrest progression of pulmonary lesions because of their low speeds of absorption and deposition and low levels of concentration in the target organ. Another problem is that the frequent use of antibacterial agents is courting an increasing incidence of bacteria resistant to such drugs.

As the above discussion on the prior art indicates, there is no impeccable prophylactic/therapeutic modality for swine pleuropneumonia because of the lack of a drug capable of finding its way into the target organ in an effective concentration and be retained there for a sufficiently long time. There accordingly exists a true need for development of a safe drug capable of controlling this diseases with certainly and without cross-resistance with the conventional drugs.

The inventors of the present invention endeavored to overcome the above-mentioned problems through earnest research and found that certain esters of bicozamycin, which are represented by the formula (I), are very effective against swine pleuropneumonia and can be used with expectation of complete cure and without cross resistance with the conventional drugs. The present invention has been developed on the basis of the above finding.

The bicozamycin ester (I) is a known compound [acylated WS-4545 substance; Japanese Patent Application Kokai No. 39497/1973] obtainable by esterifying bicozamycin [same as WS-4545 substance which is produced by certain microorganisms of the genus Streptomyces (Japanese Patent Publication No. 29158/1973)]. Bicozamycin, which is a starting material for the production of this compound (I) is known as an antibiotic produced by *Streptomyces sapporonensis* ATCC 21532 as described in Japanese Patent Publication No. 29158/1973 referred to above.

This producer strain is available from: Depository organ: American Type Culture Collection Address: 12301 Parklawn Drive, Rockville, Md., U.S.A. Date of deposit: Apr. 21, 1970 Accession number: ATCC 21532

This prophylactic/therapeutic composition for swine pleuropneumonia can be prepared either by processing compound (I) into a dosage form such as a powder, dust, microfine granule, granule, fine granule, injection, tablet, liquid, pellet or syrup with or without a solid, semi-solid or liquid vehicle or diluent or by supplementing an animal diet with said compound (I) or said dosage form.

The mode of use in which the bicozamycin ester is admixed with feedstuffs is now described in some detail. The feedstuff may be any animal food commonly used in animal husbandry, thus inclusive of various formulated feeds. An exemplary ration includes some or all of such components as corn, rice, baked wheat, wheat flour, Hokuyo meal, powdered soybean oil, yeast, milo, soybean cake, cottonseed cake, wheat bran, defatted rice bran, fish meal, skim milk powder, dry whey, oil and fat, alphalpha meal, calcium carbonate, tricalcium phosphate, sodium chloride, choline chloride, vitamins (e.g. vitamin A, vitamin D, vitamin E, vitamin $B_1$, vitamin $B_2$, vitamin $B_6$, vitamin $B_{12}$, calcium pantothenate, nicotinamide, folic acid, etc.), amino acids [e.g lysine, methionine, etc.), trace inorganic salts (e.g. magnesium sulfate, iron sulfate, copper sulfate, zinc sulfate, potassium iodide, cobalt sulfate, etc.) and so on.

The vehicle for use in the production of said various dosage forms includes all the ordinary vehicles such as water, lactose, rice bran, sucrose, glucose, starch, talc, acid clay and so on.

The dosage and duration of administration of this prophylactic/therapeutic composition for swine pleuropneumonia are dependent on the severity of the swine disease, body weight of swine, and other factors. Generally, however, a daily dose of 1 to 10 mg as bicozamycin ester (I) is administered per kg swine body weight for about 1 to 14 days.

This therapeutic/prophylactic composition for swine pleuropneumonia is a new type of drug which is different from the conventional drugs (antibacterial agents) [It should be noted that the bicozamycin ester (I) as such is not antibacterial in vitro]. Yet it is conducive to complete cure of swine pleuropneumonia and, in addition, can be used safely without cross-resistance with the conventional drugs.

The following test examples are further illustrative of the effect of the invention.

Among the compounds used in the various examples, compounds 1 and 2 and bicozamycin have the following structures.

|            | R in formula (I)    |
|------------|---------------------|
| Compound 1 | Benzoyl             |
| Compound 2 | Cyclohexanecarbonyl |
| Bicozamycin| Hydrogen            |

TEST EXAMPLE 1 (THE TIME COURSES OF BLOOD AND ORGAN CONCENTRATIONS IN SWINE)

Materials and method

Test animals:

Nine Kenborrow cross-bled swine raised on an affiliated farm of Kyoto Animal Science R & D Center and approximately 70 days after birth were used. The average body weight of swine at the test was 19.1 kg (standard deviation 1.55 kg).

Dosage and administration:

Compounds 1 and 2 and bicozamycin were administered once in a dose of 10 mg (potency) as bicozamycin/kg.

For administration, compounds 1 and 2 were each suspended in water and the suspension was administered by gastric gavage, while bicozamycin was dissolved in distilled water and the solution was administered intramuscularly (the femoral muscle).

Sampling intervals and sites:

The animals were bled to death 1, 3 and 6 hours after medication and the liver, kidneys, lungs and blood were isolated. The levels of bicozamycin in the respective tissues were determined by HPLC. As to blood, the concentrations of compounds 1 and 2 were also determined.

Results
Unit: $\mu g/ml$ (g)

| Test Substance | Tissue | | Time after administration | | |
|---|---|---|---|---|---|
| | | | 1 hr | 3 hr | 6 hr |
| Bicozamycin | Blood | Bicozamycin | 2.85 | 0.97 | — |
| | Liver | Bicozamycin | 2.97 | 1.20 | 0.55 |
| | Kidney | Bicozamycin | 2.22 | 1.86 | 0.94 |
| | Lung | Bicozamycin | 0.69 | 0.58 | 0.59 |
| Compound 1 | Blood | Bicozamycin | 3.67 | 5.68 | 1.99 |
| | | Compound 1 | 1.11 | 0.86 | — |
| | Liver | Bicozamycin | 5.88 | 3.30 | 3.55 |
| | Kidney | Bicozamycin | 5.67 | 5.28 | 6.68 |
| | Lung | Bicozamycin | 1.19 | 1.45 | 3.23 |
| Compound 2 | Blood | Bicozamycin | 5.91 | 6.46 | 1.52 |
| | | Compound 2 | 0.15 | — | — |
| | Liver | Bicozamycin | 6.67 | 2.26 | 1.39 |
| | Kidney | Bicozamycin | 4.74 | 4.57 | 2.39 |
| | Lung | Bicozamycin | 0.97 | 0.86 | 1.10 |

It was found that compounds 1 and 2 are each absorbed in the unchanged form and, then, gradually converted to bicozamycin in the body. It was also found that when compounds 1 and 2 are administered, the concentrations of bicozamycin in the organs are comparatively higher and longer-sustained.

TEST EXAMPLE 2 (A THERAPEUTIC EXPERIMENT IN SWINE WITH ARTIFICIALLY INDUCED PLEUROPNEUMONIA)

Materials and Method

Test animals: Fifty-five 10-week-old triple-cross pigs (LWB) raised on an affiliated farm of Kyoto Animal Science R & D Center and showing an aggregation antibody titer to Actinobacillus pleuropneumoniae of not more than 1:8 were used. The mean body weight of the animals at the beginning of the experiment was 20.6 kg (standard deviation 1.16 kg).

Housing and feeding: The animals per group were housed in drain board (120 x 140 cm)-floored cages in a window-less pigsty. The diet was a piglet feed (SDS No. 3) not supplemented with any antibacterial agent [of the same composition as the feed used in Example 1). Both the feed and drinking water were available ad libitum.

Challenging bacteria: A serotype II SPH-1 strain of *Actinobacillus pleuropneumoniae* (allotted by Institute of Fermentation Research) was inoculated into the nasal cavity of each animal using 5 ml of a $2 \times 10^8$ cells/ml suspension.

Trial period: The test swine were assigned to groups 7 days before infection and observed daily till day 7 after infection. All the animals were sacrificed on the last day of observation. The administration of the test compound was started 2 days before infection and continued till day 7 after infection (day of autopsy).

Examination items:

(Body weight) Determined on three occasions: first dosing, infection and autopsy (Food consumption) Measured on a group basis (Clinical signs) The animals were observed daily for body temperature, vitality, appetite, breathing, cough and posture and each finding other than body temperature was scored on the following scale.

| Vitality   | (0: normal, 1: weak, 2: emaciated) |
| Appetite   | (0: normal, 1: partial loss, 2: complete loss) |
| Breathing  | (0: normal, 1: mild abdominal, 2: severe abdominal) |
| Cough      | (0: normal, 1: mild, 2: severe) |
| Posture    | (0: normal, 1: sternal recumbency, ventral procumbency) |

(Organ lesions) Each pig was autopsied on day 7 after infection and examined for lesions, particularly in the lungs. As to pulmonary lesions, the four items of pleural adhesion, fibrous induration (including node formation and hematoma), peribronchial lymph node enlargement, and pericardial and pleural fluid retention were scored on the following scale.

Pleural adhesion
0: No adhesion
1: Mild adhesion at 1 or 2 sites
2: Adhesion at several sites
3: Adhesion over the entire pleural cavity Fibrous induration
0: No node formation
1: Nodes sized the tip of the thumb at several sites or the affected area accounts for not more than 10% of the entire lung area.
2: Nodes sized up to a quail's egg at 1 or 2 sites or the affected area accounts for not more than 30% of the entire lung area.
3: Nodes sized larger than a quail's egg or the affected area accounts for more than 30% of the entire lung area.

Enlargement of peribronchial lymph node
0: No enlargement
1: Mild enlargement
2: Moderate enlargement and congestion/hemorrhage 3: Severe enlargement and severe congestion/-hemorrhage Retention of pericardial and pleural fluids
0: No retention
1: Mild retention
2: Moderate retention
3: Severe retention Isolation and Identification of Bacteria At autopsy, *Actinobacillus pleuropneumoniae* was isolated from the affected parts of the lungs and from the lymph nodes (peribronchial) and identified.

The bacteria were isolated using a differential medium (HI agar supplemented with chicken defibrinated blood). Colonies, 0.5-2 mm in diameter, showing β hemolysis were picked and transferred to a selective medium (nutrient agar supplemented with chicken broth) for identification. (Determination of aggregation antibody titer)

At grouping, infection and autopsy, the aggregation antibody titer was determined in all animals by the microtiter method using *Actinobacillus pleuropneumoniae* serotype II antigen.

| Test substance | Method of administration | Amount added (dose*) |
|---|---|---|
| Untreated control | — | — |
| Compound 1 | Added to feed | 200 ppm (10 mg/kg) |
| Compound 1 | Intramuscular | 5 mg/kg |
| Thiamphenicol | Added to feed | 200 ppm (10 mg/kg) |
| Tiamulin fumarate | Added to feed | 300 ppm (17 mg/kg) |
| Kitasamycin | Added to feed | 330 ppm (16 mg/kg) |
| Oxytetracycline | Added to feed | 400 ppm (17 mg/kg) |
| Amoxicillin | Gastric gavage | 10 mg/kg |
| Bicozamycin | Intramuscular | 10 mg/kg |

*: Calculated from food consumption

The results are set forth in the following table.

| Test group | Clinical score | Lesion score | Body weight gain (kg/animal) | Bacterial isolation Pulmonary lesion | Bacterial isolation Peribronchial lymph node |
|---|---|---|---|---|---|
| Untreated control | 31.2 | 4.4 | 0.1 | 100% | 100% |
| Compound 1 (200 ppm, added to feed) | 2.0 | 0.4 | 3.8 | 0 | 0 |
| Compound 1 (5 mg/kg, i.m.) | 7.2 | 1.0 | 3.1 | 20 | 20 |
| Thiamphenicol (200 ppm, added to feed) | 9.0 | 1.2 | 2.6 | 60 | 60 |
| Tiamulin fumarate (200 ppm, added to feed) | 20.2 | 4.0 | 2.4 | 60 | 40 |
| Kitasamycin (200 ppm, added to feed) | 9.8 | 1.2 | 2.5 | 40 | 40 |
| Oxytetracycline (200 ppm, added to feed) | 14.8 | 1.8 | 2.2 | 60 | 40 |
| Amoxicillin (200 ppm, added to feed) | 21.2 | 2.0 | 1.4 | 60 | 60 |
| Bicozamycin (10 mg/kg, i.m.) | 8.6 | 1.0 | 3.1 | 40 | 40 |

(Note) The larger the Weight gain, the better. For the other items, the smaller, the better.

TEST EXAMPLE 3 (AN ANTI-SETTLEMENT TEST IN SWINE WITH ARTIFICIALLY INDUCED PLEUROPNEUMONIA)

Five pigs per group were artificially infected with *Actinobacillus pleuropneumoniae* and the bacteria were isolated from the peribronchial lymph node of each animal 5 days after infection.

The strain of challenging bacteria used for artificial infection was a serotype II SPH-1 strain of *Actinobacillus pleuropneumoniae* (allotted by Institute of Fermentation Research) and this strain was inoculated into the nasal cavity of each animal using 5 ml of a $2 \times 10^8$ cells/ml suspension.

Twenty 10-week-old Kenborrow cross-bled swine raised on an affiliated farm of Kyoto Animal Science R & D Center and showing an aggregation antibody titer to *Actinobacillus pleuropneumoniae* of not more than 1:10 were used. The mean body weight of the animals was 21.5 kg.

For administration, compounds 1 and 2 were each dissolved in drinking water and the solution was administered by gastric garage once a day for 5 days.

Bicozamycin was dissolved in distilled water and the solution was administered intramuscularly once a day for 3 days.

The results are set forth in the following table.

| Test group | No. of test swine | Bacterial isolation from the peribronchial lymph node |
|---|---|---|
| Untreated control | 5 | 100% |
| Compound 1 (20 mg/kg) | 5 | 0 |
| Compound 2 (20 mg/kg) | 5 | 0 |
| Bicozamycin (20 mg/kg) | 5 | 40 |

TEST EXAMPLE 4

Materials and Methods

* The study including untreated control was blinded to investigators.

Test animals: Thirty 10-week-old triple-cross pigs (LWB) raised on an affiliated farm of Kyoto Animal Science R & D Center and showing an aggregation antibody titer to *Actinobacillus pleuropneumoniae* of not more than 1:8 were used. The mean body weight and the standard deviation at the beginning of the experiment was as follows.

| Mean body weight | Standard deviation |
| --- | --- |
| 23.6 kg | 3.14 kg |

Housing and feeding: The animals per group were housed in drain board (120×140 cm)-floored cages in a reinforced ALC window-less pigsty. The diet was a piglet feed (SDS No. 3) not supplemented with any antibacterial agent. Both the feed and drinking water were available ad libitum.

Challenging bacteria: A serotype II SPH-1 strain of *Actinobacillus pleuropneumoniae* (allotted by Institute of Fermentation Research) was inoculated into the nasal cavity of each animal using 2 ml of a $2 \times 10^8$ cells/ml suspension.

Trial period: The test swine were assigned to groups 7 days before infection and observed daily till day 19 after infection. Finally, all the animals were autopsied.

The administration of the test compound was started 2 days before infection and continued till day 5 after infection.

Examination items:

(Body weight) Determined in all animals at the first dosing, at the end of dosing, 7 days after dosing and at autopsy (14 days after dosing)

(Food consumption) Measured on a group basis (Clinical signs) The animals were observed daily for body temperature, vitality, breathing, cough, posture, etc. However, the body temperature after completion of dosing was measured on days 12 and 19 after infection. Each finding other than body temperature was scored on the following scale.

| | |
| --- | --- |
| Vitality | (0: normal, 1: weak, 2: emaciated) |
| Appetite | (0: normal, 1: partial loss, 2: complete loss) |
| Breathing | (0: normal, 1: mild abdominal, 2: severe abdominal) |
| Cough | (0: normal, 1: mild, 2: severe) |
| Posture | (0: normal, 1: sternal recumbency, ventral procumbency) |

(Organ lesions) Each pig was autopsied on day 19 after infection and examined for lesions, particularly in the lungs.

As to pulmonary lesions, the four items of pleural adhesion, fibrous induration (including node formation and hematoma), peribronchial lymph node enlargement, and pericardial and pleural fluid retention were scored on the following scales.

Pleural adhesion
0: No adhesion
1: Mild adhesion at 1 or 2 sites
2: Adhesion at several sites
3: Adhesion over the entire pleural cavity Fibrous induration
0: No node formation
1: Nodes sized the tip of the thumb at several sites or the affected area accounts for not more than 10% of the entire lung area.

Enlargement of peribronchial lymph node
0: No enlargement
1: Mild enlargement
2: Moderate enlargement and congestion/hemorrhage
3: Severe enlargement and severe congestion/hemorrhage Retention of pericardial and pleural fluids
0: No retention
1: Mild retention
2: Moderate retention

Isolation and Identification of Bacteria

At autopsy, *Actinobacillus pleuropneumoniae* was isolated from the affected parts of the lungs and from the lymph nodes (peribronchial) and identified.

The bacteria were isolated using a differential medium (HI agar supplemented with chicken defibrinated blood). Colonies, 0.5–2 mm in diameter, showing $\beta$ hemolysis were picked and transferred to a selective medium [nutrient agar supplemented with chicken broth) for identification.

Determination of Aggregation Antibody Titer

At infection and autopsy, the aggregation antibody titer was determined in all animals by the microtiter method using *Actinobacillus pleuropneumoniae* serotype II antigen.

The results are set forth in the following table.

| Test group, dose | | Method of administration | Duration of administration | Weight gain | Clinical score | Lesion score | Result of bacteriological examination | |
| --- | --- | --- | --- | --- | --- | --- | --- | --- |
| | | | | | | | Pulmonary lesion | Peribronchial lymph |
| Untreated control | | — | — | 6.6 kg | 36.8 | 5.4 | 100% | 100% |
| Chlortetracycline | 500 ppm group | Added to feed | 7 days beginning 2 days before infection | 13.5 | 4.4 | 0.8 | 0 | 0 |
| Compound 1* | 38 ppm group | Added to feed | 7 days beginning 2 days before infection | 14.2 | 1.4 | 0.4 | 0 | 0 |
| Compound 1* | 75 ppm group | Added to feed | 7 days beginning 2 days before infection | 14.8 | 1.2 | 0.2 | 0 | 0 |
| Compound 1* | 150 ppm group | Added to feed | 7 days beginning 2 days before infection | 15.1 | 1.0 | 0.2 | 0 | 0 |

*: The dose is in Bicozamycin potency.
(Note) The larger the weight gain, the better. For the other items, the smaller, the better.

EXAMPLE

The following example is further illustrative of the invention.

EXAMPLE

A powder is prepared by mixing 1.3 parts by weight of compound 1 [a compound of formula (1) wherein R is benzoyl] with 98.7 parts by weight of rice bran.

The object of preventing and curing pleuropneumonia of swine can be accomplished by mixing 400 g of the above powder with 30 kg of the following ration and administering the mixture to 20 animals weighing 20 kg on the average or a total of 400 kg daily for 7 days.

| Ration | |
|---|---|
| Component materials | Corn, baked wheat, wheat flour, bran, soybean cake, Hokuyo meal, skim milk powder, glucose, sucrose, purified beef tallow powder, soybean oil powder, alphalpha meal, yeast, vitamins, minerals, amino acids and flavor. |
| General ingredients | Crude protein 17.2%, crude fat 3.7%, crude fiber 3.5%, crude ash 4.9%, calcium 0.96%, phosphorus 0.77%, digestible crude protein 14.0%, total digestible nutriment 75.2%, digestible |

| Ration |
|---|
| energy 331 Cal/100 g. |

We claim:

1. A method for therapy of swine pleuropneumonia characterized by dosing swine with an effective amount of a compound of the following formula:

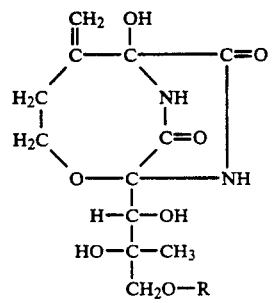

wherein R means a benzoyl group or a cyclohexanecarbonyl group as an active ingredient in admixture with a vehicle.

2. A method for therapy of swine pleuropneumonia according to claim 1 wherein R means a benzoyl group.

* * * * *